United States Patent [19]

Sutter

[11] 4,447,209
[45] May 8, 1984

[54] IMPLANT FOR SECURING A DENTURE
[75] Inventor: Franz Sutter, Niederdorf, Switzerland
[73] Assignee: Institut Straumann AG, Switzerland
[21] Appl. No.: 319,080
[22] Filed: Nov. 6, 1981
[30] Foreign Application Priority Data
   Aug. 20, 1981 [CH] Switzerland ............... 5375/81
[51] Int. Cl.³ .............................................. A61C 8/00
[52] U.S. Cl. ...................................................... 433/173
[58] Field of Search ................ 433/173, 176, 174, 175
[56] References Cited
   U.S. PATENT DOCUMENTS
   2,835,033  5/1958  Airosser ........................ 433/173
   4,180,910  1/1980  Staumann ....................... 433/173
   4,195,367  4/1980  Kraus ............................ 433/173
   FOREIGN PATENT DOCUMENTS
   2302715 10/1976 France ............................. 433/173

Primary Examiner—Robert Peshock
Attorney, Agent, or Firm—McGlew and Tuttle

[57] ABSTRACT

An implant is disclosed for securing a base to be anchored in a jaw bone and formed by two substantially cylindrical hollow sleeves open on both their ends, and an also hollow portion of a pin. The other portion of pin projecting beyond the base forms a column intended for supporting a denture. The outer surfaces of the sleeves are provided with grooves which are distributed over the circumference. At the side remote from the column, the grooves do not extend up to the respective end face of the sleeve, so that at these locations the grooves shallow out by end faces which are capable of transmitting axial pressures occurring in an implant inserted in a jaw. The grooves also contribute to a uniform circumferential distribution of forces which are to be transmitted in a direction transverse to the column axis. With the sleeves open also on the column side, only little bone material over growth is needed for covering the sleeves.

25 Claims, 15 Drawing Figures

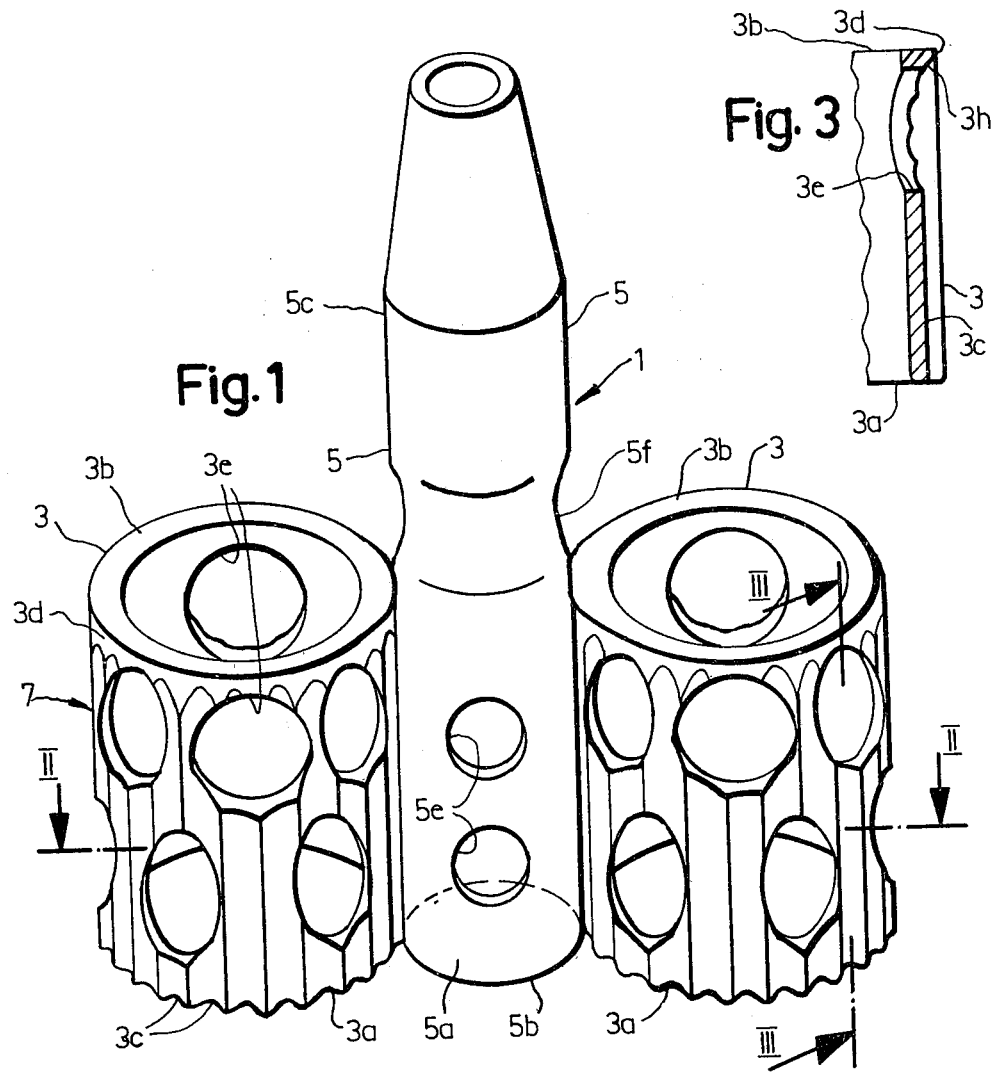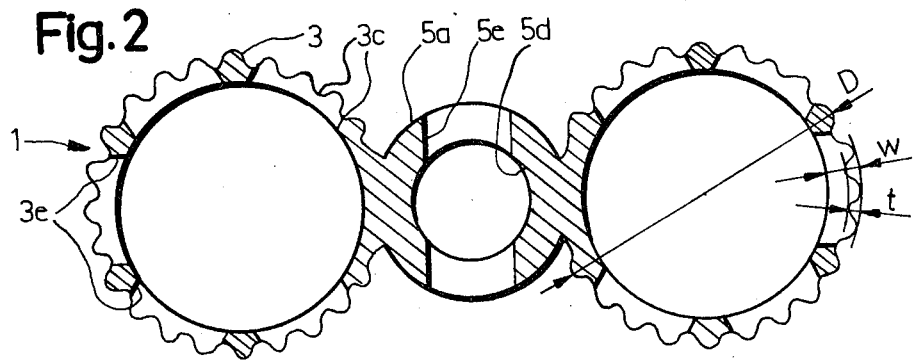

IMPLANT FOR SECURING A DENTURE

FIELD AND BACKGROUND OF THE INVENTION

The invention relates, in general, to an implant and, more particularly, an implant for securing a denture to a jaw bone of the type having a base to be inserted into the bone and at least one column for supporting the denture with the base including at least one substantially hollow-cylindrical part which is open at a side remote from the column.

Swiss Pat. No. 604674 discloses a jaw implant comprising a sleeve-like base having a substantially circular cylindrical wall and a front wall closing one end of the sleeve. At this front wall, the base is connected to a column, while on its other end, the base is open. Circumferentially distributed bores are provided in the cylindrical wall and in the transition zone between this wall and the front wall. A rib extends helically on the outer surface of the cylindrical wall.

Swiss Pat. No. 618870 and the corresponding U.S. Pat. No. 4,180,910 disclose jaw implants having a base of two or three sleeve-like, substantially regular cylindrical parts, and a column which is connected by one end to the base and projects to its other end intended for supporting a denture, beyond the hollow-cylindrical base parts. The hollow, circularly-cylindrical base parts are entirely open on their ends remote from the column, but have front walls on their other ends. The cylindrical and front walls of the sleeve-like base parts are provided with bores having a diameter which is substantially smaller than the inside diameter of the sleeve-like base parts.

If an implant in accordance with one of the aforecited three references is inserted in a jaw, considerable forces must be transmitted, for example, during biting. Forces or force components both in the longitudinal direction of the column and transverse thereto may occur. Particularly, the forces acting transversely to the column may produce very high local loads capable of causing and developing resporption of the bone material. This happens, especially, in instances where the implant base comprises a single sleeve-like part or where the forces act on two or three sleeve-like parts of an implant base in a plane passing substantially through the axes of the two, or of all of the base parts.

Implants of the above-mentioned kind are inserted into the jaw so deeply that even the front wall of the hollow-cylindrical base part or parts is embedded in the bone and comes to lie slightly below the initial bone surface. To make such an insertion possible, a hole is milled into the bone for each of the hollow-cylindrical base parts, the hole has a deep portion in the form of an annular gap for receiving the wall of the hollow cylinder, and a shallow, fully cylindrical portion for receiving the front wall thereof. Upon inserting the implant, the bone grows, in, over the front wall or walls again so that eventually only the column projects from the bone.

A rather large amount of bone material must thus be removed in the shallow areas where the holes receive the front walls of the bases. This, of course, is undesirable, especially with an implant to be inserted into the upper jaw. That is, in the upper jaw, the corticalis, that is, the layer of relatively solid bone material, is thin as compared to the corticalis of the lower jaw. Consequently, with holes as described above made in the upper jaw, the implant is held in place by the porous spongiosa alone. That is why it is frequently impossible to obtain a satisfactory anchoring in the upper jaw.

SUMMARY OF THE INVENTION

The invention is primarily directed to an implant in which the forces to be transmitted are distributed as far as possible uniformly, even if the occurring forces are crosswise of the longitudinal axis of the column. Further, the design of the implant is to allow a stable and permanent anchoring even in a bone having a relative thin corticalis.

In accordance with the invention, this is obtained by providing an implant of the above mentioned kind, wherein the cylindrical wall of the substantially hollow cylindrical part is provided with recesses and/or elevations which extend or are arranged along stright lines parallel to the longitudinal axis of the column.

Particularly advantageous developments of the invention are characterized in that the recesses and/or elevations are provided on the outer cylindrical surface of the wall, characterized in that at least ten grooves are provided which are distributed over the circumference of the hollow-cylindrical part and form the recess, characterized in that the recesses are formed by grooves which open by one of their ends into the end face remote from the column of the hollow-cylindrical part and are limited on their other end by the end faces, characterized in that considered in a cross-section perpendicular to the longitudinal direction of the column, the recesses as well as the elevations therebetween, and the transition between the recesses and the elevations, are smoothly rounded and characterized in that the recess augment the respective cylindrical suface area by at least 50 percent, as compared to a truly cylindrical surface area.

The invention further relates to an implant in accordance with the hollow-cylindrical parts completely open even on their ends turned to the column.

Advantageous developments of the implant include an arrangement in which a substantial circularly-cylindrical part is aligned with the column, and further characterized in that the base includes only parts which are substantially circularly cylindrical, and have their axes of rotational symmetry extending parallel to each other, and which are tangent to, or intersect, each other, and characterized in that all the circularly cylindrical parts included in the base are hollow and open on their ends remote from the column.

Thus, in accordance with the invention, there is provided an implant for securing a denture to a jaw bone comprising a base to be inserted into the bone and at least one column for supporting the denture, the base including at least one substantially hollow-cylindrical part open at the side remote from the column, said substantially hollow-cylindrical part having a cylindrical wall with at least one of recesses and elevations which extend along straight lines parallel to the longitudinal axis of the column.

Accordingly, it is an object of the invention to provide an implant for securing a denture to a jaw bone which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 1 is a perspective view of an implant;

FIG. 2 is a sectional view taken along the line II—II of FIG. 1.

FIG. 3 is a sectional view taken along the line III—III of FIG. 1;

DETAILED DESCRIPTION

Figure 4:
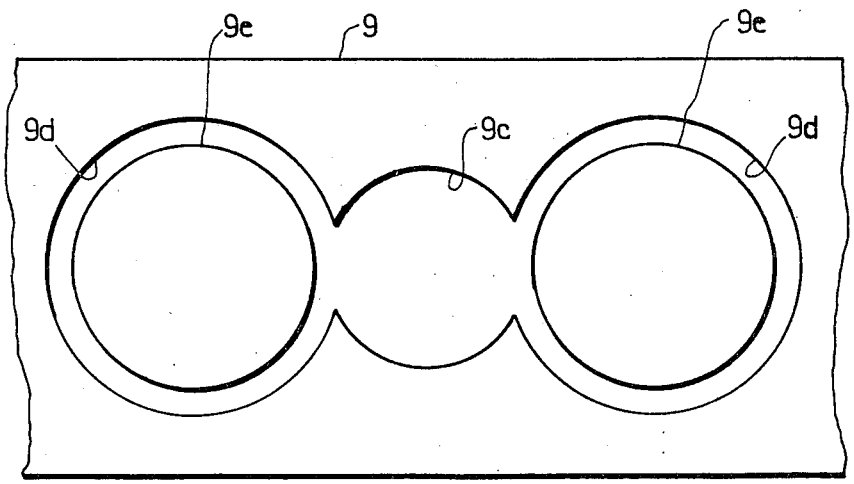
FIG. 4 is a bottom plan view of an upper jaw.

FIGS. 1 and 2 show an implant, generally designated 1, for securing a denture to a jaw or jaw bone. Implant 1 is made from a metal, such as titanium, and includes two sleeves 3, having substantially the shape of circular cylinders. Sleeves 3 are open on both their ends, so that they only comprise each a cylindrical wall bounded by radial end faces 3a,3b, without any cover or bottom. In other words, the sleeves have a circularly cylindrical hole of constant cross-section extending therethrough in the direction of the central axis or axis of rotational symmetry thereof from a first open end to a second open end. A substantially rotationally symmetrical pin 5, having its central or longitudinal axis, or axis of rotational symmetry, extending in parallel with, and in the same place as, the axis of rotational symmetry of sleeves 3 is also provided. Pin 5 is disposed centrally between the two sleeves 3.

A portion 5a of pin 5 is rigidly connected to the two sleeves 3, such as by welding, or is made integrally therewith. In the contact area between pin portion 5a and sleeves 3, the cylindrical walls of the sleeves intersect with portion 5a, or at least fit one another snugly. End face 5b of pin portion 5a is flush with the respective end faces 3a of sleeve 3. The two sleeves 3 and pin portion 5a form together a base 7 intended to be anchored in a jaw bone. A portion of pin 5 projects beyond end faces 3b or sleeves 3 and forms a column 5c for supporting a denture.

The outer surface of each of sleeves 3 is provided with at least ten and, for example, twenty grooves 3c which extend parallel to the central axes of sleeve 3 and pin 5 and, except for the area of contact with pin 5, are uniformly distributed over the circumference of the sleeves. Grooves 3c form recesses and, along with the lands, ribs, or ridges therebetween, result in a serrated cross-sectional configuration. In cross sections perpendicular to the sleeve axes, both grooves 3c and the ridges, as well as all of the transition areas, therebetween, are smoothly rounded. Grooves 3c open into the end faces 3a of sleeves 3, however, on their other ends, they do not extend up to end faces 3b. As shown in FIG. 3, shortly before end face 3b, grooves 3c shallow out into the outer cylindrical envelope by curved end faces 3h. A smooth cylindrical surface strip 3d is thus formed between end face 3b and ends of grooves 3c, as shown in FIG. 1. A number of through holes 3e is provided in sleeves 3, which are distributed over the cylindrical walls. The holes are formed by bores which have a diameter exceeding the width of grooves 3c, and thus partly interrupt the grooves. As compared to a smooth cylindrical surface, grooves 3c enlarge the outer surface area of the sleeve walls.

The maximum outer diameters D and the lengths or heights of sleeves 3 are approximately equal to each other and of a magnitude of five to six millimeters, for example. The thickness W of the sleeve walls and thus the radial width of end faces 3b is at least 7% and at most 15%, for example about 10%, of the maximum outer diameter D. This means that the minimum wall thickness W is about 0.35 mm and the maximum is about 0.9 mm, and may be 0.5 to 0.6 mm, for example. Grooves 3c are by about 0.1 to 1. mm shorter than sleeves 3. The depth t of grooves 3c may be 30% to 70%, preferably 40 to 60%, of the wall thickness W, thus about 0.1 to 0.3 mm. Shape and dimensions of the grooves are generally provided so as to increase the outer surface area of the sleeve all by 50%, for example, as compared to an apertured smooth surface without grooves.

Pin portion 5a is hollow, and the circularly cylindrical cavity 5d extends from pin end face 5b up to the level of sleeve end faces 3b. Pin portion 5a is thus also designed as a sleeve which, however, is open only on its end remote from column 5c. The wall of pin portion 5a is also perforated, by bores or holes 5e. The outer diameter of pin portion 5a is the largest diameter of pin, which, however, is smaller than sleeve diameter D, and may amount to 2.5 to 3.5 mm, for example.

In the proximity of sleeve end face 3b, column 5c may be provided with a neck 5f smoothly merging into the adjacent portions of pin 5. The free end portion of column 5c tapers conically toward the end.

Figure 5:
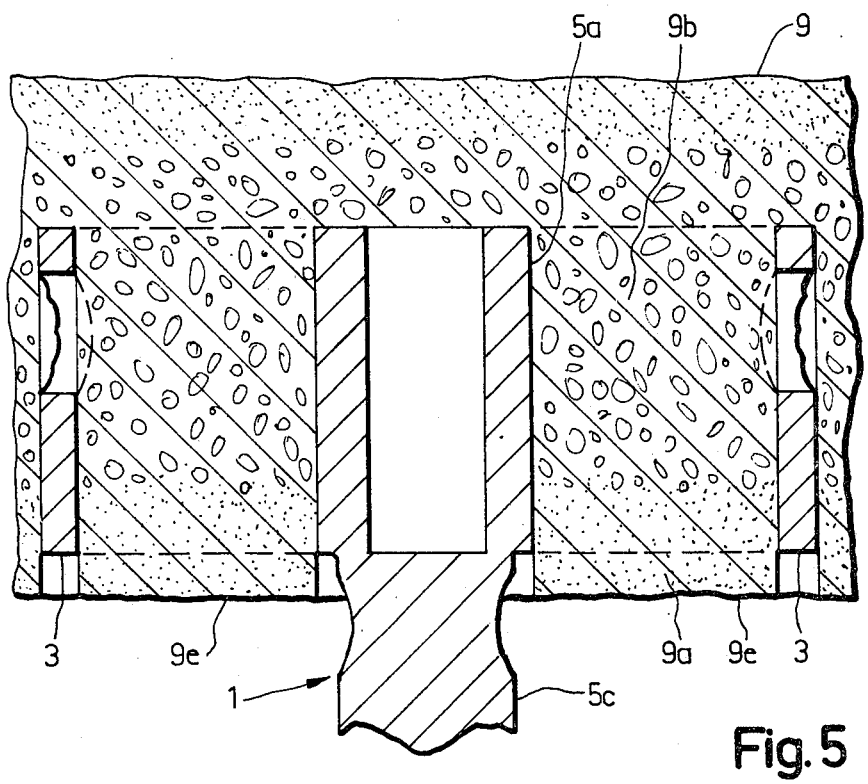
FIG. 5 is a schematic sectional view of a bone as shown in FIG. 4, immediately after the insertion of an implant.
Figure 6:
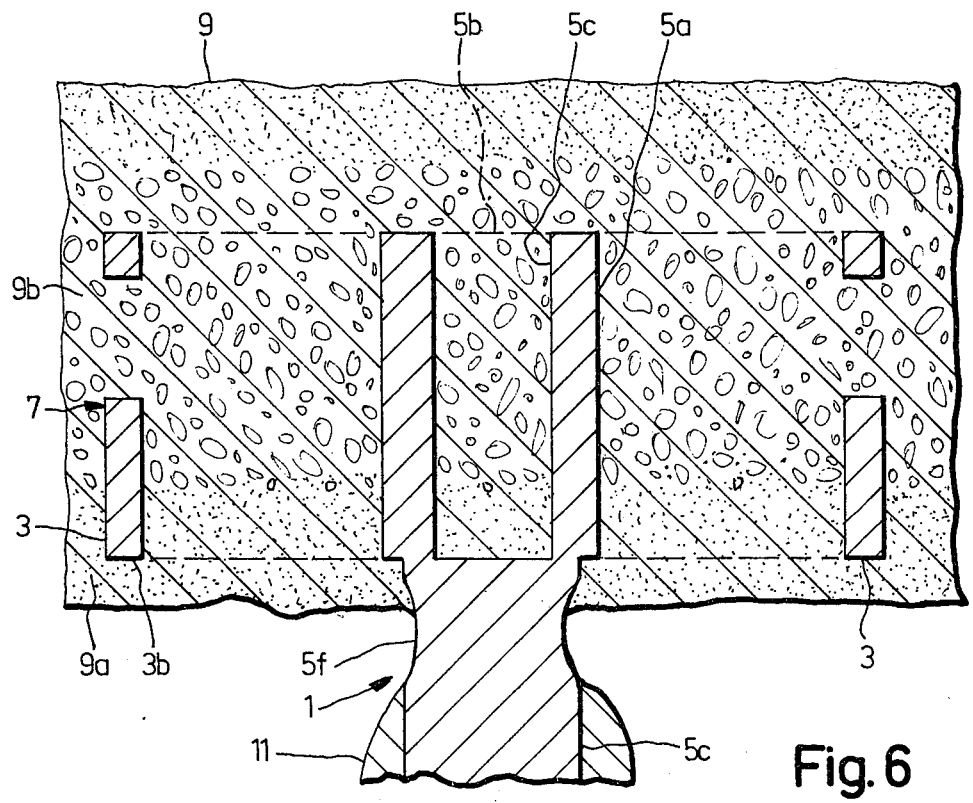
FIG. 6 is a sectional view corresponding to FIG. 5, after some time period, that is, after the bone has grown through and over the implant.
Figure 7:
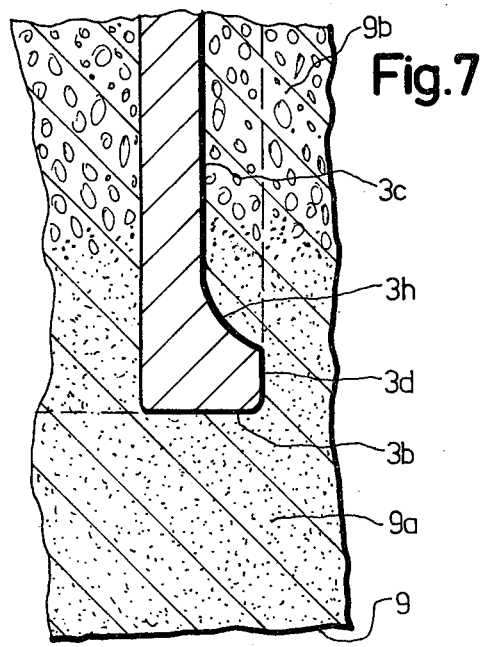
FIG. 7 is an enlarged sectional view of another portion of a base implanted in an upper jaw bone.

FIGS. 4, 5 and 6, illustrate a portion of an upper jaw bone 9. In an upper jaw bone, the relatively compact and stable corticalis 9a forms a rather thin boundary zone. The interior of the bone is a relatively porous spongiosa 9b, the transition between these two structures of the bone being more or less continuous. In FIGS. 5, 6 and 7, the corticalis is indicated by stippling, and the spongiosa as a coarse grain.

To insert an implant 1 into an upper jaw, initially the soft tissues (not shown) are removed as far as necessary, and the upper jaw bone 9 is exposed. Then, first, a full-diameter bore 9c is milled in bone 9, having a diameter corresponding to that of pin portion 5a which will later be received therein. Temporarily, a gage plug is inserted in bore 9c. Then, with the aid of this plug, two annular grooves 9d are drilled or milled into the bone, in which sleeves 3 will be received. In surgery, such annular grooves 9d are frequently termed trephined or trapan bores. The inner diameter of annular grooves 9d is approximately equal to the inner diameter of sleeves 3. The outer diameter of annular grooves 9d is approximately equal to the outer diameter D of the sleeves, and preferably smaller by the depth t of grooves 3c, so that to introduce the base, sleeve 3 must be forced in and the bone material penetrates into grooves 3c already at the insertion of the implant. The depth of annular grooves 9d is dimensioned so as to embed sleeves 3 in bone 9 completely but to have the sleeve portions and grooves 3c adjacent end faces 3b still located in the corticalis 9a, as particularly clearly shown in FIG. 5.

Consequently, at the time the implant is inserted into a bone 9, bone studs 9e are still present which penetrate and fill out the cavity of sleeve 3 and, preferably, even protrude some therefrom. Upon inserting implant 1, the bone material grows through holes 3e, 5e and also over the annular end faces 3b of the sleeves. Further, the bone material grows into grooves 3c except that it has been forced therein already during the insertion. After the regeneration and growth of the bone, base 7 is completely embedded in and penetrated by the bone material, as shown in FIGS. 6 and 7. To cover sleeves 3, relatively little further growth of the bone material is sufficient, since only end faces 3b are to be overgrown. Therefore, base 7 of the implant is completely covered by the bone material within a relatively short time after inserting the implant, except for pin portion 5a connected to column 5c. The soft tissues (not shown in FIGS. 4 to 7) surrounding the bone also regenerate and grow into neck 5t. Then, a denture 11 such as a bridge, can be secured to column 5c.

After bone 9 is, so to speak, grown into base 7, the curved end faces 3h of grooves 3c are embedded in the corticalis. These end faces contribute to an effective transmission of forces acting in the longitudinal direction of column 5c, to the bone, since they bear against the corticalis which, as mentioned above, is more compact and stable than the spongiosa.

Figure 8:
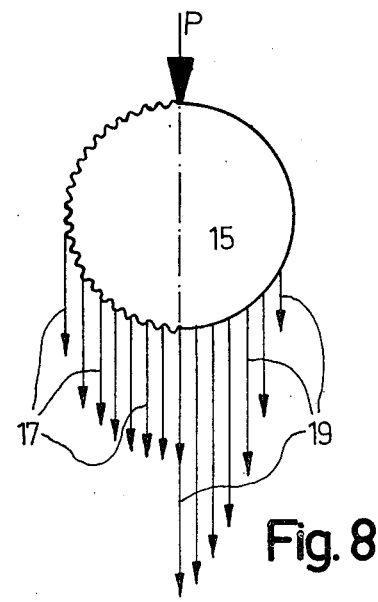
FIG. 8 is a diagram showing the transfer of forces on the circumferential surface of a cylindrical base part, with, for comparison, a serrated surface with the respective force distribution being shown at the left, and a smooth surface at the right.

Furthermore, grooves 3c are very important to the transmission of forces acting on column 5c transversely. FIG. 8 is intended to illustrate how a force P acting crosswise of the axis of symmetry of column 5c is transmitted from bone 9 to a sleeve 3 after the bone is grown into grooves 3c as explained above. Force P is assumed to act in a direction perpendicular to the axis of rotational symmetry of sleeve 3, or parallel to this direction. In the left half of FIG. 1, the serrated circumference of sleeve 3 is shown. Even at a location which is remotest from the diameter 15, the flanks of the respective ribs form faces which are not parallel to the direction of force P and form therewith angles between about 45° and 135°. This makes sure that forces are still transmitted from the bone to sleeve 3 and vice versa even at locations which are remotest from diameter 15. The force P, to be transmitted, is split into components which are distributed as indicated by vector arrows 17. In this way, the force P to be transmitted is distributed over a large portion of the circumference of sleeve 3 relatively uniformly. The faces bounding holes 3e, 5e also contribute to this transmission of forces of course. This results in a uniform local distribution of forces and loading of the bone material.

With the outer surface of the sleeve being a smooth cylindrical surface, the distribution of the force components would be such as indicated in the right hand half of FIG. 8 by arrows 19. The sleeve locations remote from diameter 15 would remain substantially ineffective in the transmission of a force P.

Figure 9:
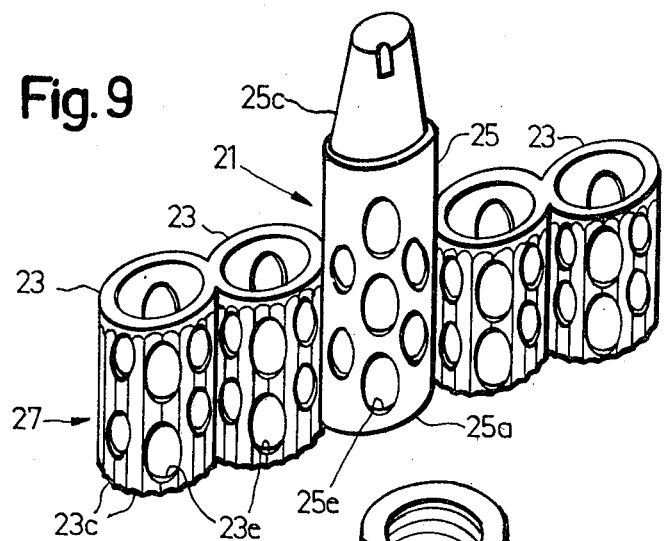
FIGS. 9 to 13 are perseptice views of alternate implant embodiments.

The implant shown in FIG. 9 includes a substantially hollow-cylinder sleeves 23 which are open on both ends and similar in design to sleeves 3, particularly also provided with grooves 23c corresponding to grooves 3c, and with through holes 23d. Between the two inner sleeves 23, a longer pin 25 is provided having its portion 25a rigidly connected to the two adjacent sleeves 23 and forming therewith a base 27 which can be anchored in a jaw. The axes of the sleeves and of pin 25 lie in a common plane. Pin portion 25a has approximately the same diameter as sleeves 23 and is also designed as a hollow cylinder which is open on its end flush with the respective ends of the sleeves. The cylindrical wall of pin portion 25a is provided with through holes 25e. The end portion projecting beyond sleeves 23 of pin 25 forms a column 23c for supporting a denture.

Figure 10:
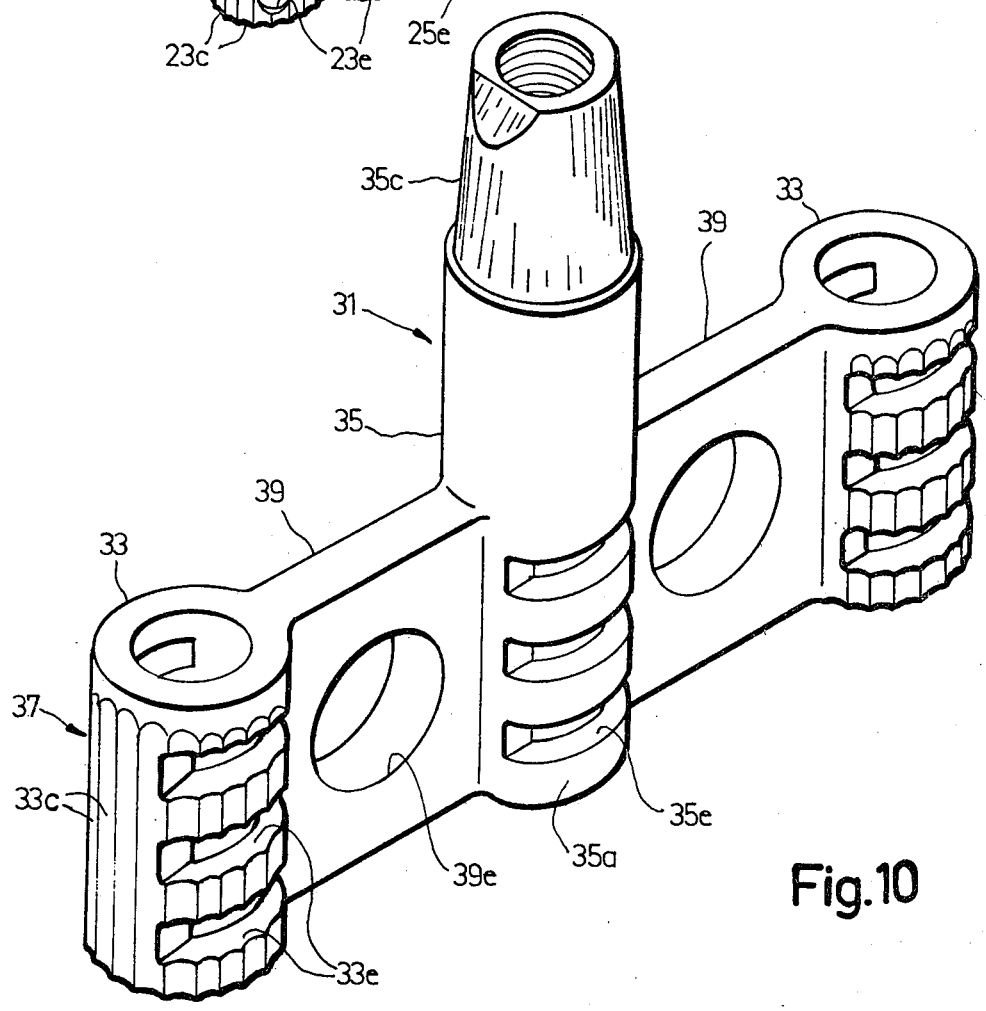

The implant 31 shown in FIG. 10 includes two hollow-cylindrical sleeves 33 which are open on both their ends and are provided with grooves 33c corresponding to grooves 3c. The cylindrical walls of sleeves 33 are provided with apertures 33e in the form of slots which extend substantially in planes perpendicular to the central axis of the sleeves. A pin 35 is provided having its portion 35a rigidly connected to sleeves 33 by webs 39, with the axes of sleeves 33 and pin 35 being parallel to one another and extending in a common plane. Sleeves 33, pin portion 35c, and webs 39 form together a base 37 to be anchored in a jaw bone. Pin portion 35a is hollow and its cylindrical wall is provided with through holes 35e in the form of slots extending crosswise of the longitudinal axis of the pin. Webs 39 are provided each with at least one circular through hole 39e. The portion protruding beyond base 37 of pin 35 forms a column 35c for supporting a denture.

Figure 11:
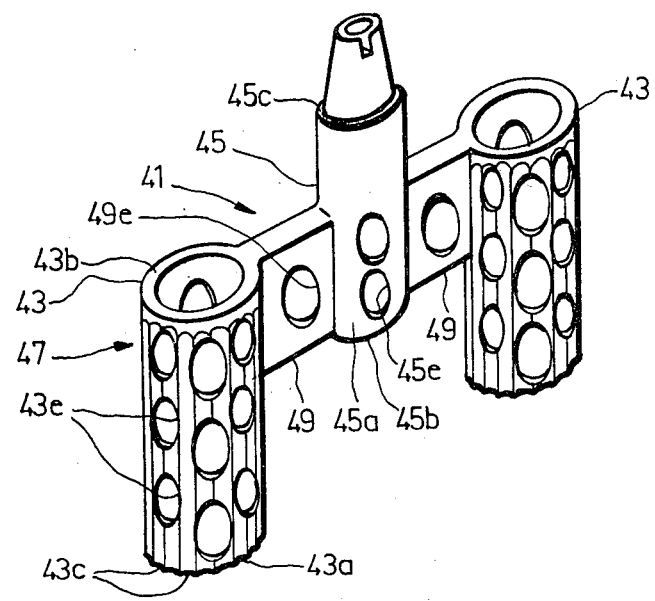

The implant 41 shown in FIG. 11 includes two hollow-cylindrical sleeves 43 which are open on both their ends and have end faces 43a, 43b, grooves 43c and circular holes 43e, and a pin 45 comprising a hollow portion 45a which is provided with circular holes 45e and connected to sleeves 43 by webs 49 having a circular hole 49e. Base 47 of implant 41 thus includes two sleeves, one pin portion, and two webs in the same way as base 37 of implant 31. However, it differs from the latter particularly in that the height of webs 49 is smaller than the height of length of sleeves 43. Webs 49 extend from end faces 43b of sleeves 43 only to about half the height of the sleeves. End face 45b of pin portion 45a is flush with the web edges which extend about at the middle of the sleeves. The portion projecting beyond base 47 of pin 45 again forms a column 45c for supporting a denture.

Figure 12:
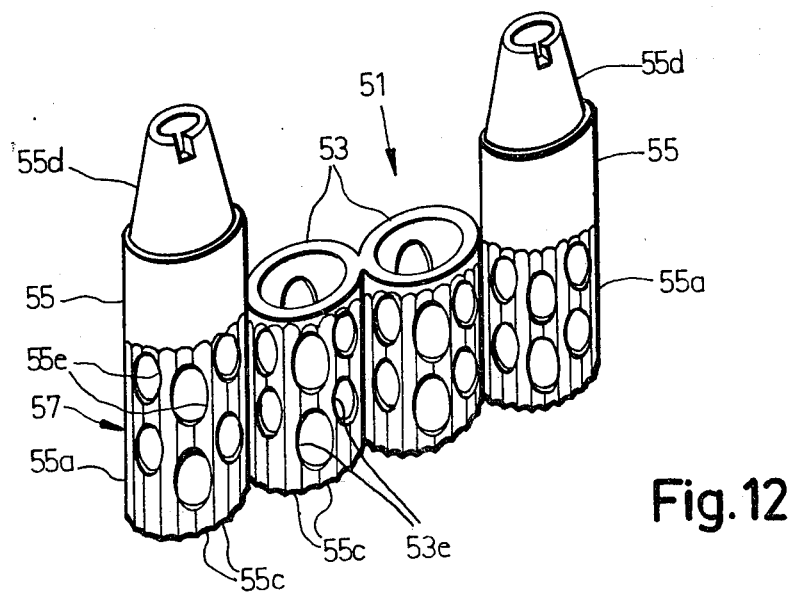

The implant 51 shown in FIG. 12 includes two hollow-cylindrical sleeves 53 which are open on both their ends. Like in sleeves 3, the cylindrical walls are provided in grooves 53c and circular holes 53e. Two pins 55 are provided, and their portions 55a form together with the two sleeves 33 the base 67 of the implant. The axes of rotational symmetry of sleeves 53 and pins 55 are parallel to each other and extend in a common plane. The two sleeves 53 are disposed between the two pins 55 and the connections therebetween are rigid. Pin portions 55a are cylindrical and hollow and provided with grooves 55c which are the same design and extension as grooves 53c. The cylindrical walls of pin portions 55 are provided with circular through holes 55e. The pin portions projecting beyond base 57 form columns 55d for anchoring a denture.

Figure 13:
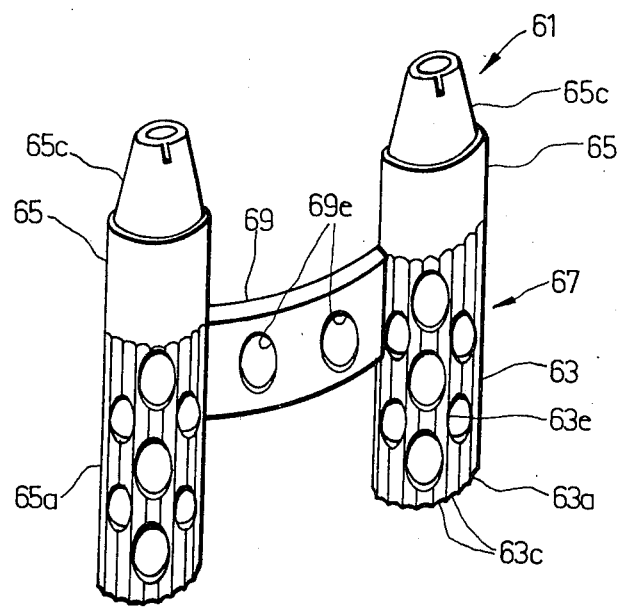

The implant 61 shown in FIG. 13 includes two pins 65 having their lower portions, as viewed in FIG. 13, designed as hollow-cylindrical sleeves 63 which are downwardly open. Sleeves 63 along with a rigid connecting web 69 form a base 67 to be anchored in a jaw bone. The pin portions shown above web 69 in FIG. 13 form columns 65c for supporting a denture. The axes of rotational symmetry of the two pins 65 are parallel to each other and lie in the same plane, while web 69 is slightly bent out of this plane. The implant is thus slightly arcuate as viewed in the direction of the pin axes. The outer surface of each of the sleeves is provided with grooves 63c distributed over the circumference. The grooves extend from the end face 63a of the sleeve up to about the level of the upper edge (FIG. 13) of web 69 where they terminate in a shallowing out curved end face. The sleeves are provided with circular through holes 63e and the web with circular through holes 69e.

Figure 14:
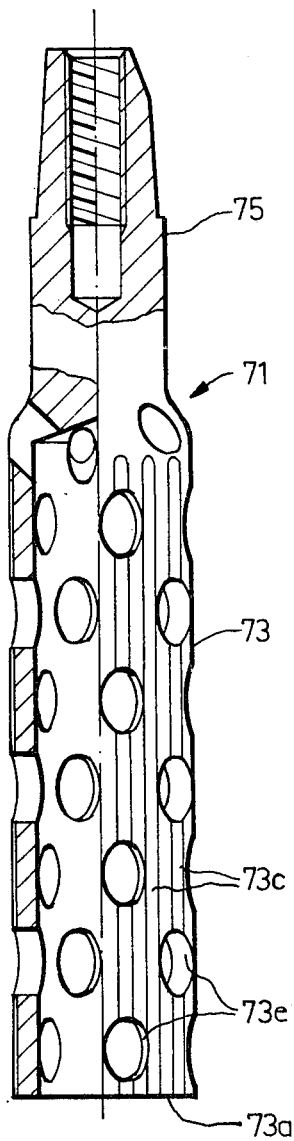
FIG. 14 is a partial, sectional view of still another embodiment of an implant.
Figure 15:
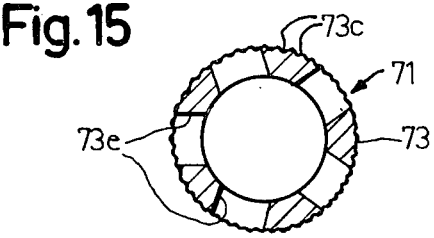
FIG. 15 is a sectional view through FIG. 14.

The implant 71 in FIGS. 14 and 15 comprises a stepped, substantially rotational symmetrical pin in one piece. The thicker portion shown below in FIG. 14 is formed by a substantially hollow-cylindrical sleeve 73 and serves as a base to be anchored in a jaw. The remaining portion of the pin forms the column 75 for supporting a denture. A preferably rounded shoulder is provided between sleeve 73 and column 75. On its side remote from column 75, sleeve 73 is open, on its other end the sleeve is closed by column 75 and the mentioned shoulder. The outside surface of the sleeve wall is provided with circumferentially distributed grooves 73c. The grooves extend parallel to the axis of rotational symmetry of implant 71, and from the radial, annular end face 73a of sleeve 73 to locations not quite adjacent the mentioned shoulder, where they terminate in curved shallowing out end faces. The cylindrical wall of sleeve 73 is provided with through holes 73e, i.e., bores, with further holes being provided in the zone of the mentioned shoulder. Column 75 is designed with a blind, tapped hole.

While implants 1,21,31,51 and 61 are suitable primarily for securing tooth bridges, implant 71 may also be used for securing individual artifical teeth.

The implants may be modified in different ways.

For example, in implants 1,21,31,41 and 51, the sleeves and columns may be displaced relative to each other to have the parallel axes extending in a curved surface.

Implants 1,21,31 and 41 may have their pin portions 5a,25a,35a,45a belonging to the base provided with grooves similar to grooves 3c.

Further, the outer surfaces of the sleeves provided with longitudinal grooves may be provided with additional grooves extending circularly or helically around the sleeves. Such additional grooves would cross with the longitudinal ones and interrupt the ridges or elevations therebetween.

Another possibility is to provide the inner surface of the sleeves with grooves extending parallel to the axis of rotational symmetry of the sleeve.

The implant can be inserted both in the upper and lower jaw. Thus, in accordance with the invention there is provided an implant for securing a denture 11 to a jaw bone 9 comprising a base 7 to be inserted into the bone and at least one column 5c for supporting the denture 11, with the base 7 including at least one substantially hollow-cylindrical part 3 which is open at the side remote from the column 5c, characterized in that the cylindrical wall of the substantially hollow-cylindrical part 3 is provided with recesses 3c or elevations, or both, which extend or are arranged along straight lines parallel to the longitudinal axis of the column.

The implant may be further characterized in that the recesses 3c and/or elevations are provided on the outer cylindrical surface of the wall.

The implant may be even further characterized in that at least ten grooves 3c are provided which are distributed over the circumference of the hollow-cylindrical part 3 and form the recesses.

The implant may be still even further characterized in that the recesses are formed by grooves 3c which open by one of their ends into the end face 3a remote from the column of the hollow-cylindrical part 3 and are limited on their other ends by end faces 3h.

The implant is preferably characterized in that considered in a cross-section perpendicular to the longitudinal direction of the column, the recesses 3c as well as the elevations therebetween, and the transitions between the recesses 3c and the elevations, are smoothly rounded.

In accordance with a preferred embodiment, the implant is still characterized in that the recesses 3c augment the respective cylindrical surface area by at least 50%, as compared to a truly cylindrical surface area.

An implant, in accordance with another embodiment of the invention for securing a denture 11 to a jaw bone 9, comprises a base 7 to be inserted in the jaw bone and at least one column 5c for supporting the denture 11, with the base 7 including at least two substantially hollow-cylindrical parts 3 which are axially parallel and are open on their sides remote from the column 5c, characterized in that said hollow-cylindrical parts 3 are completely open even on their ends turned to the column 5c. The alternate embodiment may be further characterized in that the base 7 includes a substantially circularly-cylindrical part 5a which is aligned with the column 5c. The alternatie embodiment may be even further characterized in that the base 7 includes only parts 3, 5a which are substantially circularly cylindrical, and have their axes of rotational symmetry extending parallel to each other, and which are tangent to, or intersect, each other. The alternate embodiment may be even still further characterized in that all the circularly cylindrical parts 3, 5a included in the base 7 are hollow and open on their ends from the column 5c.

Finally, in accordance with the invention, there is provided a method of securing a denture to a jaw bone, with the base of an implant comprising a column 4 supporting the denture being inserted into the jaw bone, and the base of the implant including at least two substantially circularly cylindrical, hollow sleeves which are open on both their ends, and with an annular groove being milled into the mone for each of the sleeves in such a manner that a bone stud is formed extending through the sleeve and projecting therefrom.

While specific embodiments of the invention have been shown and described in detail to illustrate the application of the principles of the invention, it will be understood that the invention may be embodied otherwise without departing from such principles.

What is claimed is:

1. An implant for securing a denture to a jawbone comprising a base to be inserted into an annular groove of the bone and at least one column for supporting the denture, said base including at least two hollow, substantially cylindrical parts each having an inner diameter and open at both ends to the same extent as said inner diameter, said hollow substantially cylindrical parts each having a substantially cylindrical wall with at least one of recesses and elevations which extend along straight lines parallel to the longitudinal axis of the column, and a plurality of apertures defined therethrough, whereby bone can grow through said apertures, said aperures intersecting said at least one of recesses and elevations.

2. An implant according to claim 1, wherein said at least one of recesses and elevations are provided on the outer cylindrical surface of said cylindrical wall to form grooves.

3. A implant according to claims 1 or 2, including at least, ten grooves distributed over the circumference of the hollow-cylindrical part, wherein said grooves form said recesses.

4. An implant according to claim 1, wherein said hollow, substantially cylindrical part has opposite end faces and wherein said recesses comprise grooves open at one of their ends into an end face remote from the column of the hollow, substantially cylindrical part, and said grooves are bound on their other ends by end faces.

5. Am implant according to claim 1, including elevations between recesses, and wherein said recesses and elevations in a cross section perpendicular to the longitudinal direction of the column, and the transitions between said recesses and said elevations are smoothly rounded.

6. An implant according to claim 1, wherein said recesses increase the respective cylindrical surface area by at least 50%, as compared to a truly cylindrical surface area.

7. An implant according to claim 1, wherein said hollow, substantially cylindrical part has opposite end faces and including recesses comprising grooves open at one of their ends into the end face remote from the column of the hollow substantially cylindrical part and said grooves being bound on their opposite ends by said opposite end faces.

8. An implant according to claims 1, or 7, including elevations between recesses, and wherein said recesses and elevations in a cross section perpendicular to the longitudinal direction of the column, and the transitions being said recesses and said elevations are smoothly rounded.

9. An implant according to claims 1, or 7, wherein said recesses increase the respective cylindrical surface area by at least 50%, as compared to a truly cylindrical surface area.

10. An implant according to claim 1, wherein said apertures have, measured along the circumference of said wall, an extent that is greater than the width of the said recesses, so that at least some of the recesses are interrupted by the apertures.

11. An implant according to claim 1, wherein said recesses have a depth (t), measured between a deepest part of said recesses and a cylindrical surface snugly fitting said wall between said recesses of at least 30% of a maximum wall thickness.

12. An implant according to claim 1, wherein all parts thereof are rigidly and unremovably connected together.

13. An implant according to claim 1, formed completely of a single integral piece.

14. An implant for securing a denture to a jawbone, comprising a base to be inserted into the jawbone and at least one column connected to said base and having a top end for supporting the denture, said base including at least two hollow substantially cylindrical parts extending axially parallel to each other open on bottom ends thereof which are remote from said column top end, said substantially cylindrical parts being open on top ends thereof adjacent said column top end, said open bottom and top ends having openings of a diameter equal to an inner diameter of said hollow parts, said cylindrical parts having a wall thickness and a length which is long with respect to said wall thickness and being tangentially joined to said at least one column along said length.

15. An implant according to claim 14, wherein said base includes a substantially cylindrical part which is aligned with said column.

16. An implant according to claims 14 or 15, wherein said base includes only parts which are substantially cylindrical, and having axes of rotational symmetry extending parallel to each other, and which are tangent to, or intersect, each other.

17. An implant according to claim 16, wherein all of said substantially cylindrical parts included in said base are hollow and open on their ends remote from said column.

18. An implant according to claim 14 formed completely of a single integer piece.

19. An implant according to claim 14, wherein said column is connected with two of said hollow substantially cylindrical parts by webs.

20. A method of securing a denture to a jawbone with an implant of the type having a base including a column for supporting the denture, and the base of the implant including at least two substantially circular cylindrical, hollow sleeves having an inner diameter and which are open on both their ends to the extent of said inner diameter for each sleeve, comprising the steps of milling an annular groove into the bone for each of the sleeves in such a manner so that a bone stud is formed for extending through the sleeve and projecting therefrom, and inserting the implant into the jawbone, with the bone stud extending into the sleeve and projecting therefrom.

21. An implant for securing a denture to a jawbone comprising a base to be inserted into an annular groove of the bone and at least one column connected to a top of said base for supporting the denture, said base comprising a hollow, substantially cylindrical part having an open bottom end which is open to the same diameter as an inner diameter of said hollow, substantially cylindrical part, said substantially cylindrical part having a plurality of grooves extending parallel to a longitudinal axis of said column and including a plurality of apertures intersecting said grooves.

22. An implant according to claim 21, including at least ten grooves distributed evenly over the circumference of said substantially cylindrical part.

23. An implant according to claim 21, wherein said column and base are formed completely of a single integral part.

24. An implant according to claim 21, wherein said apertures have, measured along the circumference of said substantially hollow part, an extent that is greater than the width of at least two of said grooves.

25. An implant according to claim 21, wherein said grooves have a depth (t), measured between a deepest part of said grooves and a cylindrical surface snugly fitting around said substantially cylindrical part of at least 30% of a maximum wall thickness of said substantially cylindrical part.

* * * * *